(12) United States Patent
Kirchner

(10) Patent No.: US 7,291,116 B2
(45) Date of Patent: Nov. 6, 2007

(54) PLEXOR

(75) Inventor: Hansjörg Kirchner, Markgröningen (DE)

(73) Assignee: Kimetec GmbH Medizintechnik, Ditzingen (DE)

(*) Notice: Subject to any disclaimer, the term of this patent is extended or adjusted under 35 U.S.C. 154(b) by 397 days.

(21) Appl. No.: 10/374,746

(22) Filed: Feb. 25, 2003

(65) Prior Publication Data

US 2004/0165375 A1 Aug. 26, 2004

(51) Int. Cl.
*A61B 19/00* (2006.01)
(52) U.S. Cl. ...................................... 600/553
(58) Field of Classification Search ................ 600/552, 600/553, 528; 606/238; 128/740; 84/457
See application file for complete search history.

(56) References Cited

U.S. PATENT DOCUMENTS 3,344,781 A * 10/1967 Allen ........................... 84/457
5,657,763 A * 8/1997 Schneider ................... 600/553
6,510,918 B2 * 1/2003 Bates .......................... 181/131
6,790,184 B2 * 9/2004 Thierman .................... 600/553

FOREIGN PATENT DOCUMENTS

DE 91 03 170 U1 7/1991

* cited by examiner

Primary Examiner—Max F. Hindenburg
Assistant Examiner—Fangemonique Smith
(74) Attorney, Agent, or Firm—Pauley Petersen & Erickson

(57) ABSTRACT

A plexor having a handle and a head attached to a front section, and having tapping elements seated on both sides on a receiving body. One tapping element terminates in a line-shaped tapping section, and the other tapping element terminates in a point-like tapping section. An orientation of the line-shaped tapping section can be rotated into different angular positions around an axis extending in the longitudinal direction of the head and can be fixed in place in the desired rotated position.

18 Claims, 5 Drawing Sheets

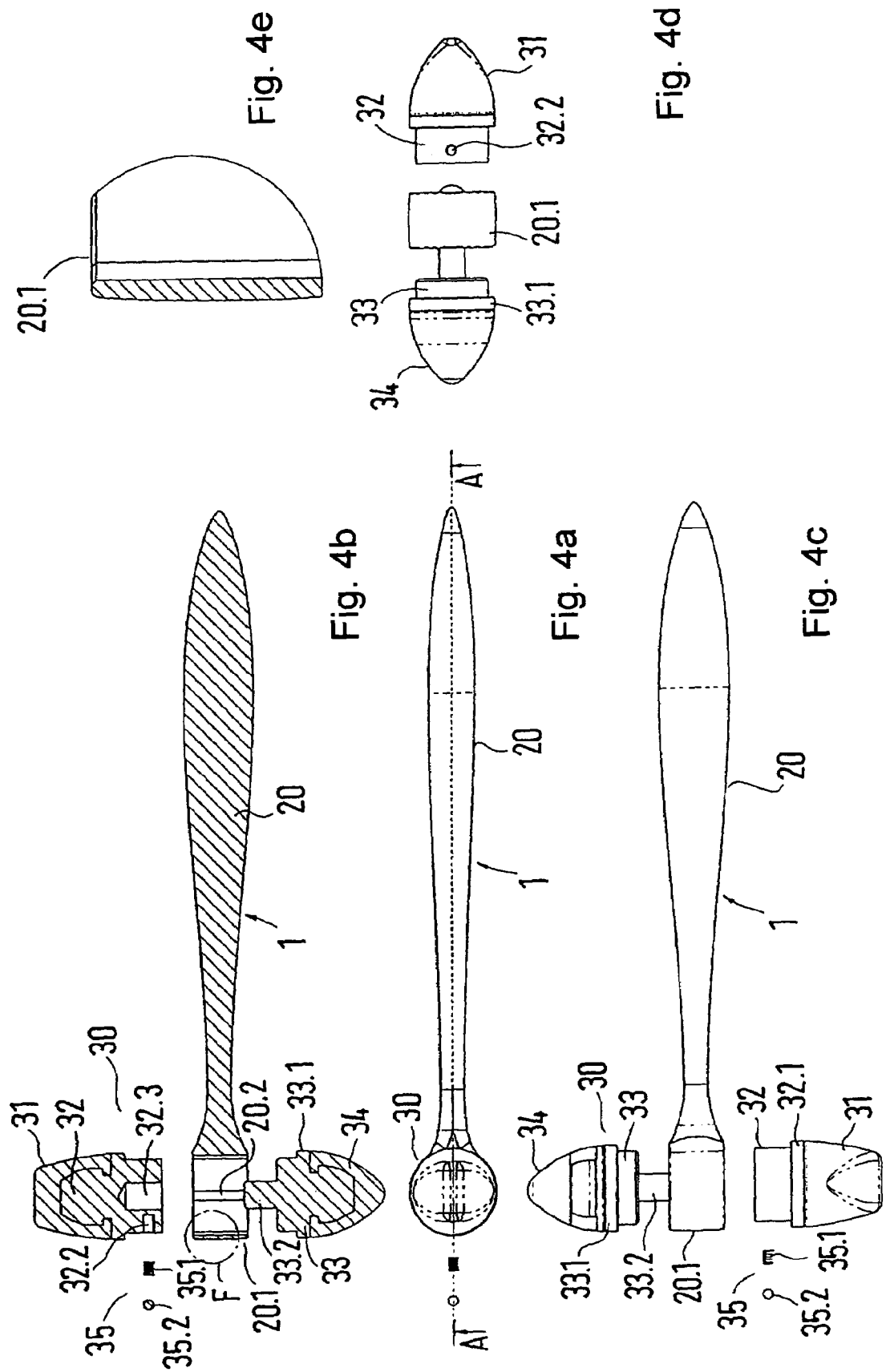

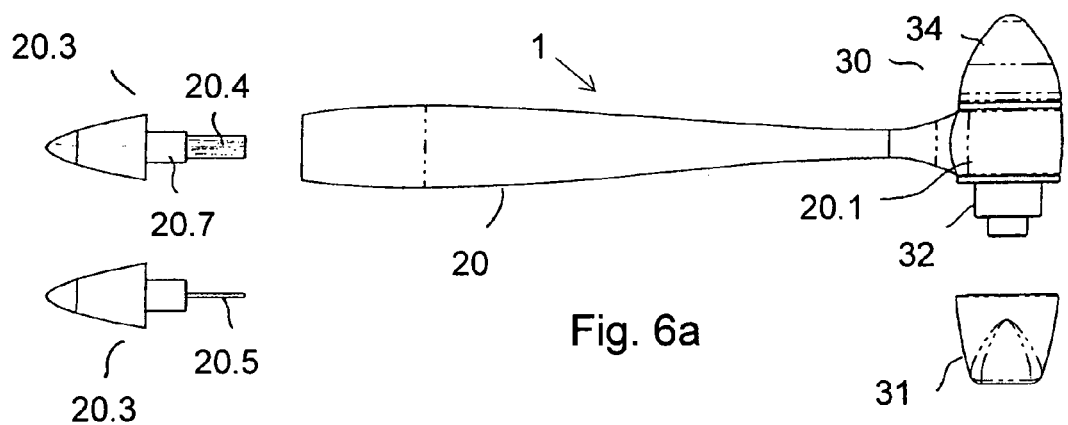
Fig. 6a
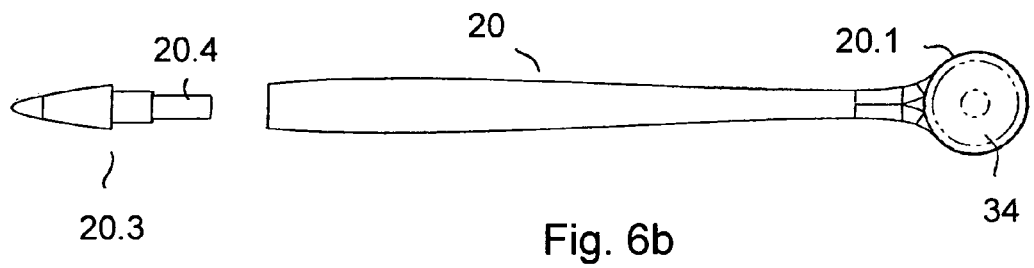
Fig. 6b
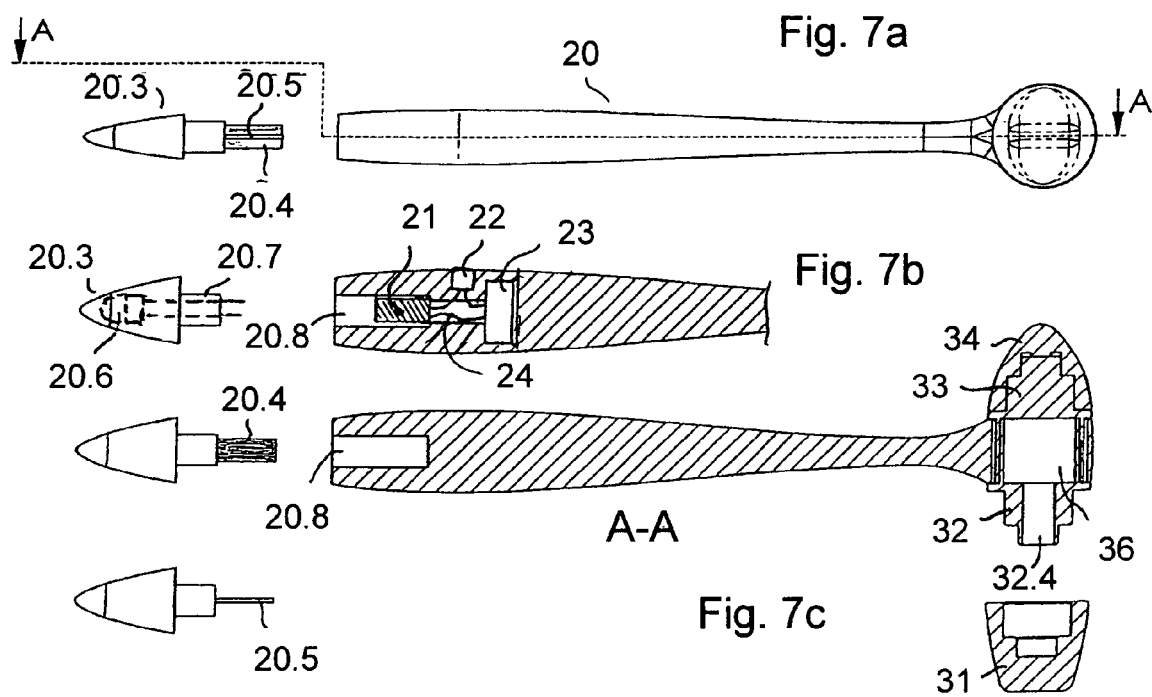
Fig. 7a
Fig. 7b
Fig. 7c

PLEXOR

BACKGROUND OF THE INVENTION

1. Field of the Invention

This invention relates to a plexor with a handle and a head attached to a front section, having tapping elements seated on both sides on a receiving body.

2. Discussion of Related Art

A plexor is taught by German Patent Reference DE 91 03 170 U1. A center element with two protruding pins of a head with a threaded bore is screwed on a threaded front section of a handle of this known plexor. Tapping bodies are placed on each of the pins, and are fixed in place in the pins by annular grooves and have tapping sections, with ends bent to different degrees.

SUMMARY OF THE INVENTION

One object of this invention is to provide a plexor of the type mentioned above but with more employment options and simple handling.

This object is achieved according to characteristics described in this specification and in the claims. A tapping element terminates in a line-shaped tapping section, and an other tapping element in a point-like tapping section. An orientation of the line-shaped tapping section can be rotated into different angular positions around an axis extending in a longitudinal direction of the head and can be fixed in place in the desired rotated position.

Thus, the expression "line-shaped tapping section" is intended to relate to the radius of curvature vertically with respect to the line being considerably less than the radius of curvature in the direction of the line which, for example, can be infinite such as when a straight line. Because of the rotatability and option of fixing it in place in the desired rotated position, the plexor can be used in an easily manipulable manner in various positions for performing the tapping motion.

In certain embodiments, there is a clamping mechanism or a snap-in mechanism for fixing the tapping section in place.

In other embodiments, the one tapping element can be rotatably seated in relation to the fixed receiving body or is seated together with it for fixing in place.

A simple, stable design, along with simple operation, results because the receiving body has a rotationally symmetrical center section. The front section of the handle has a ring-shaped holding section with an axis that extends transversely in relation to the handle, in which the center section is rotatably received and in which it can be fixed in place.

The various rotated positions can be simply and unequivocally selected because depressions are cut on the inner circumference of the holding section at predetermined angular positions, which are engaged by at least one snap-in element which, in the appropriate rotated position, is seated on the receiving body and is resiliently pushed outward, wherein the depressions have and/or the snap-in element has beveled or rounded flanks.

In another embodiment, for fixing the rotated position, the clamping mechanism has a screw, which is fixed on the holding section, by which the inner radius of the ring can be reduced, or which can be turned through the ring for support on the receiving body.

Further characteristics are advantageous for a solid design and simple assembly, wherein the receiving body is assembled from two partial receiving bodies, one of which has an axially oriented central holding pin, and the other which has a holding bore matched to it, and wherein the two partial receiving bodies are connected with each other, at least in the area of the holding pin and holding bore, by being pressed together, screwed or glued together. Thus, the receiving body can be simply attached to the ring-shaped holding section.

In one embodiment, the plexor has a line-shaped tapping section that can at least be fixed parallel with respect to a plane formed between the handle and the head and at right angles to it.

In one advantageous step, the ring-shaped holding section is formed on the handle.

Regarding the weight distribution, and an advantageous manipulation connected therewith, and with the structure, the receiving body is made of metal and has two detent rings, which are arranged in a standardized way in relation to the longitudinal axis of the head and are spaced apart from each other, and has a circumferential side flush with the respectively adjoining circumferential side of the tapping elements.

The rotation and fixing in place of the line-shaped tapping section in the desired position of rotation can also occur in steps wherein re-plugging means are provided for rotating and fixing the line-shaped tapping section in place.

In another embodiment for complementing the employment options of the plexor, a hollow space is formed in the head, into which at least one function element is inserted or can be inserted.

In this case the design can be such, for example, that the at least one function element is at least a weight element and/or an illumination unit. With the weight element the user can adapt the manipulation at will and with the illumination unit the user can trigger a pupil reflex, for example, or can examine the tongue or the throat area, or the like, of a patient.

In housing options for the function element, the hollow space is arranged at least partly in the interior of the holding section and/or a receiving body.

In one construction, along with advantageous manipulation, the illumination unit has an electrical energy supply unit and a light source. A manually operable switching member, which is integrated into the head, is interspersed in a connecting line between the energy supply unit and the light source. The light source is oriented for emitting light in the direction of a head element. For illuminating an object, the head element can be removed or is transparent. For a low energy consumption and a rugged construction it is particularly advantageous if the light source has a light-emitting diode. The light spectrum can then be selected in a manner suitable for the intended use.

In other embodiments, the function element is a brush, a single fiber or a light which, in the inserted state of the end element, can be connected to an electrical energy source inserted into the handle and can be manually switched on via a switching element arranged on the handle.

BRIEF DESCRIPTION OF THE DRAWINGS

This invention is explained in view of exemplary embodiments, in view of the drawings, wherein:

FIGS. 4a to 4e show different views of the plexor of FIG. 3, but with a partially disassembled head, and additionally a portion F as shown in FIG. 4b;

FIGS. 6a, 6b, 7a, 7b and 7c show different views of the plexor with function elements integrated into the handle.

DESCRIPTION OF PREFERRED EMBODIMENTS

Figure 1:
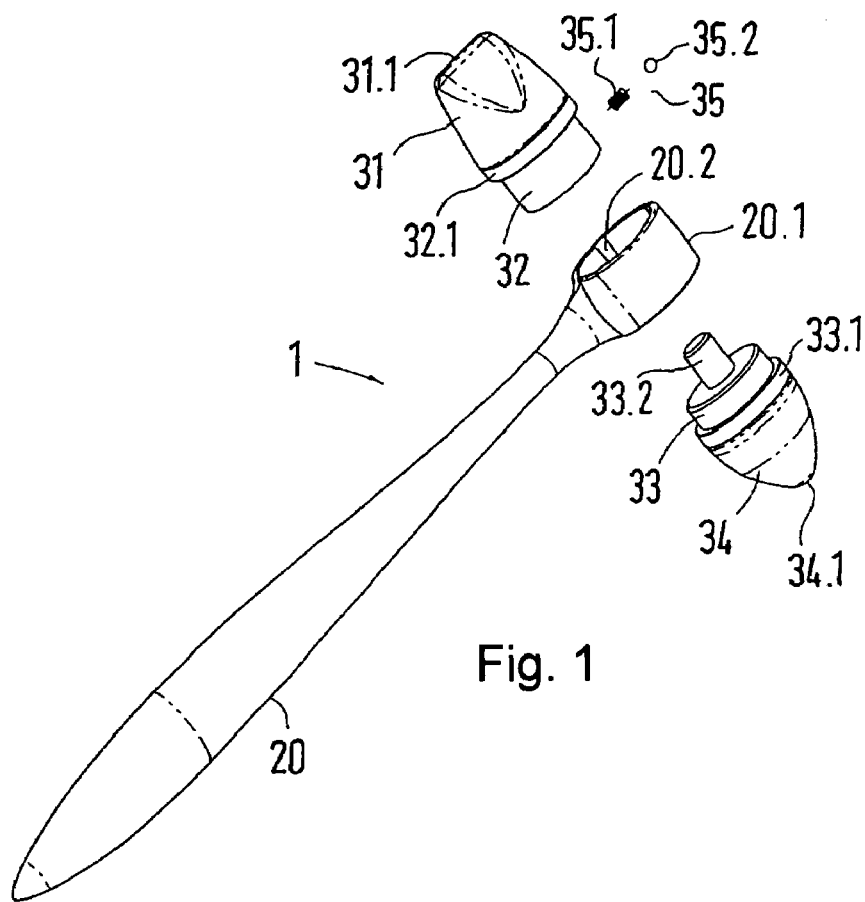
FIG. 1 is a perspective plan view of a plexor in a partially disassembled state.
Figure 2:
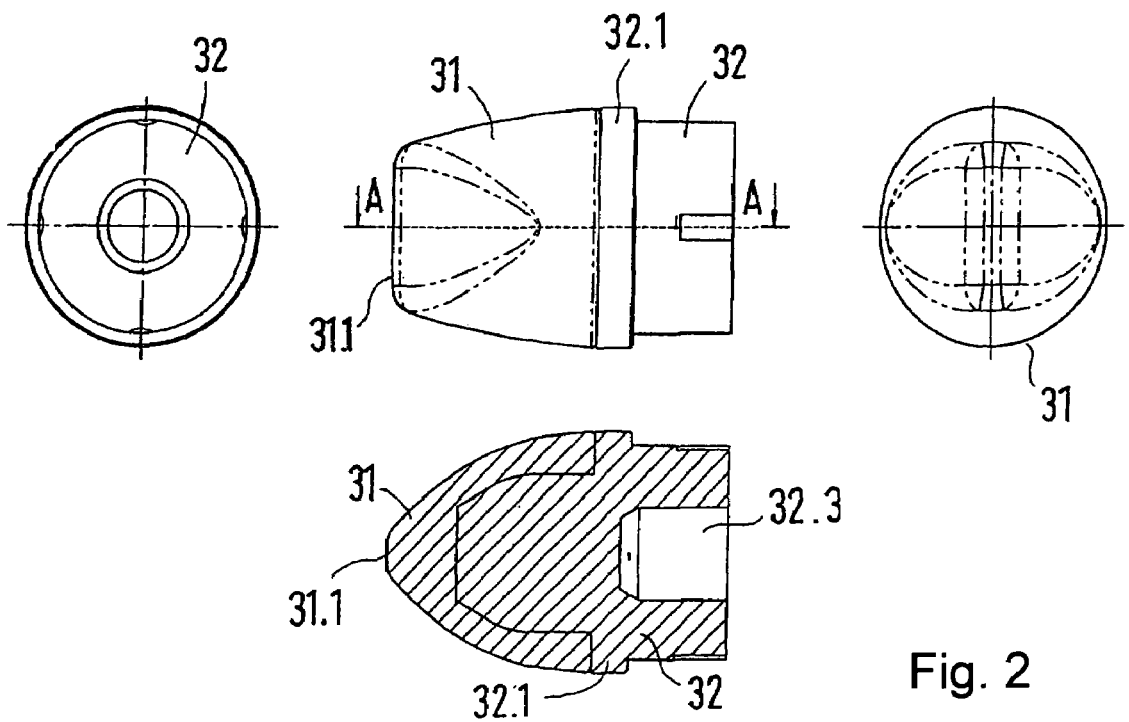
FIG. 2 shows different views of a portion of the plexor shown in FIG. 1.
Figure 3D:
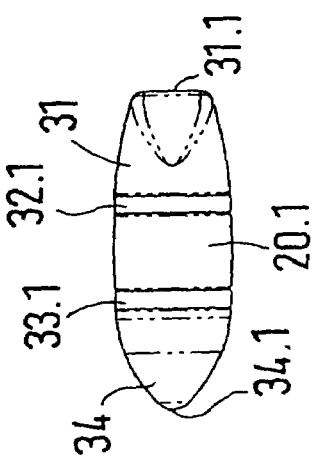
FIGS. 3a to 3d show the plexor of FIG. 1, respectively, in a lateral view in a direction from above on the head, in a sectional view along a line A-A shown in partial FIG. 3a, in a lateral plan view of a lateral representation of the head, and in a front view from the direction of the head.
Figure 3B:
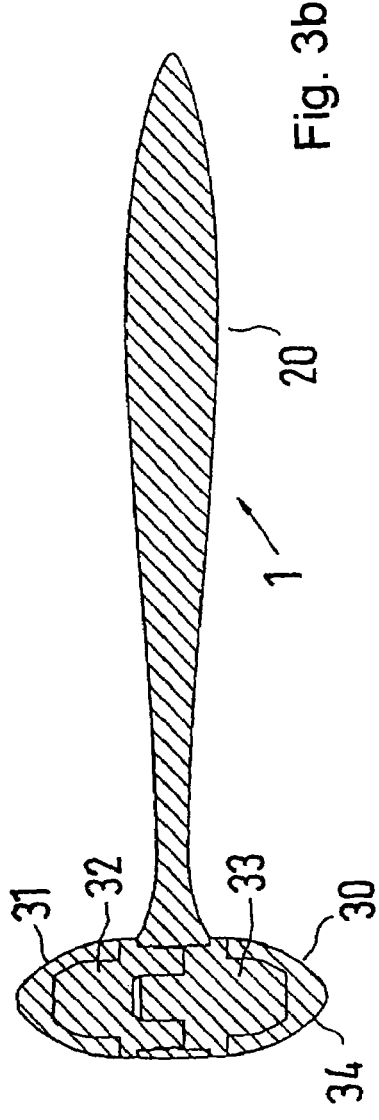
Figure 3A:
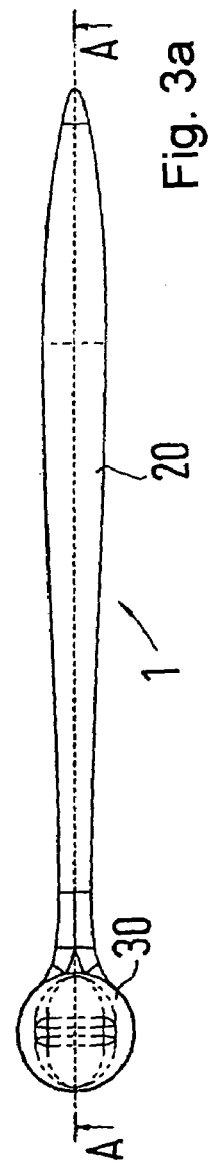
Figure 3C:
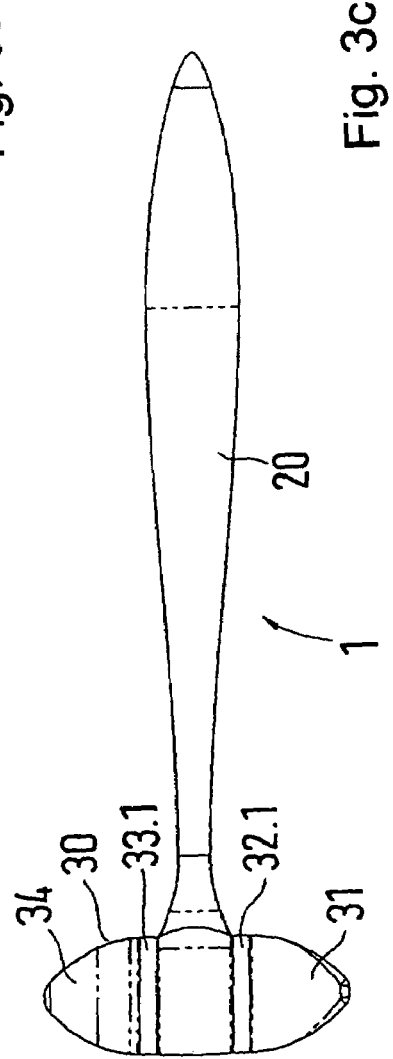

As shown in FIG. 1 and FIGS. 3a to 3d and FIGS. 4a to 4e, a plexor 1 has a handle 20 and a head 30, which is arranged in the front section of the handle 20, vertically with respect to it and has a tapping element 31 or 34 on each side. The two tapping elements 31, 34 are attached to the respective partial receiving bodies 32 or 33, which are seated in a ring-shaped holding section 20.1 and are plugged into each other. The one tapping element 31 has a line-shaped tapping section 31.1, while the other tapping element 34 has a more point-like, rotationally-symmetrically rounded tapping section 34.1. The line-shaped tapping section 31.1 can be straight along the line or curved slightly convex toward the outside, for example in the shape of a hatchet, with a relatively large radius of curvature, while transversely to the line it is formed in a wedge shape or rounded with a very small radius of curvature. The handle 20 is preferably formed from plastic and can have a metal insert. The tapping elements 31, 34 are also preferably formed of plastic or rubber, while the partial receiving bodies 32, 33 are preferably embodied as metal bodies, for an advantageous weight distribution for manipulating the plexor 1. On their sides facing the partial receiving body 32 or 33, the tapping elements 31, 34 have a hollow space with beads at the edges, by which they are plugged onto corresponding protrusions with circumferential grooves of the partial receiving body 32, 33 and maintained on them.

The one partial receiving body 32 has a central holding bore 32.3, whose wall can have slits in the sides, so that a certain amount of widening is possible for stably plugging in and maintaining a matched holding pin 33.2 of the other partial receiving body 33. Adjoining the ring-shaped holding section 20.1, the two partial receiving bodies 32 and 33 each have a detent ring 32.1 or 33.1, whose outer diameter preferably corresponds to the ring-shaped holding section 20.1, and also to the outer diameters of the attached tapping elements 31 or 34 which adjoin the other side of the detent ring 32.1 or 33.1. This results in a stable clear construction, from which the metal core of the receiving body extends visible from the outside.

The one partial receiving body 32, which has the holding bore 32.3 and with its outside adjoins the inside of the ring-shaped holding section 20.1, has on its outside a receiving bore 32.2 for receiving an arresting means 35 with an inside-located spring 35.1 and an outside-located snap-in element 35.2, which is shown in FIG. 4b, for example. On the inside of the ring-shaped holding section 20.1, axis-parallel grooves 20.2 are cut, for example offset from each other by an angle of rotation of 90° or 45°, into which the partial receiving body 32 snaps at the appropriate rotational position. Thus, the line-shaped tapping section 31.1 of the tapping element 31 can be set in a simple way by rotating the head 30, for example with the line-shaped tapping section 31.1 parallel with the plane defined by the head 30 and the handle 20, or vertically with respect to it. Other suitable rotated positions are also conceivable. The groove 20.2 extending to the edge of the ring-shaped holding section 20.1 makes a simple insertion of the snap-in element 35.2 possible during assembly.

Further employment possibilities can be accomplished with the structures in accordance with FIGS. 5, 6a, 6b, 7a, 7b and 7c.

Figure 5:
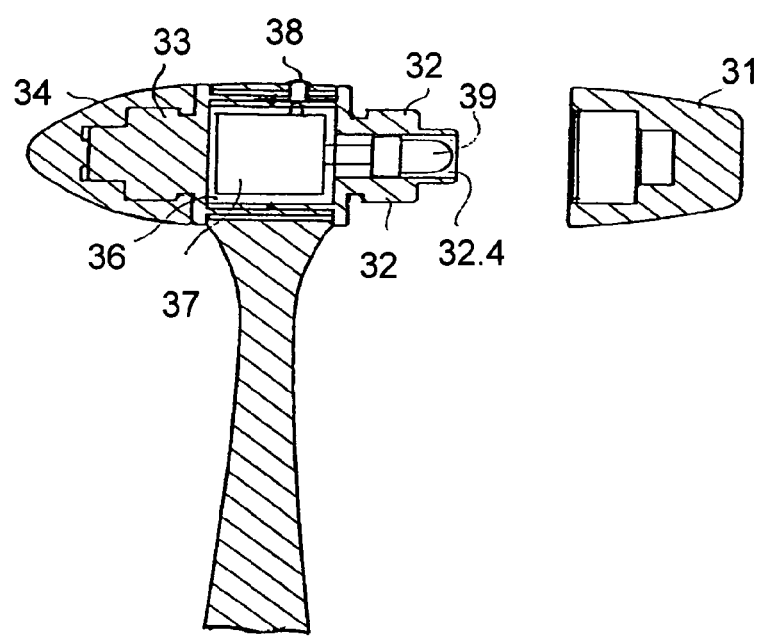
FIG. 5 shows an exemplary embodiment of the plexor with a function element integrated into the head.

In accordance with FIG. 5, a hollow space 36 is formed in the head 30, inside of the interior bordered by the detent ring 32.1, in which at least one body 37 is received and fixed in place. For example, the body 37 includes at least one exchangeable weight element, by which the manipulation of the plexor 1 can be varied at will by the user. The fixation can be provided, for example, by clamping, snapping in or screwing the body 37 into corresponding counter elements of the hollow space 36.

The body 37 can also be a part of an illumination unit, in particular a set of batteries or rechargeable batteries for the energy supply for a light 39, in particular in the form of a light-emitting diode (LED), which is arranged and fixed in place in a through-bore 32.4 adjoining the hollow space 36 and arranged in the partial receiving body 32 or 33 so that it emits light in the axial direction of the head 30. For illuminating an object, either the associated head element 31 or 34 is removed, or it is made of a transparent material. A switching member 38, for example a key, which can be manually activated from the outside, is provided in the connecting line between the light 39 and the electrical supply unit, and is also integrated into the head 30, for example in the ring-shaped holding section 20.1.

In another option for housing and designing the switching member 38, it is actuated by twisting the rotatably seated head element 31 or 34 or by twisting the partial receiving body 32 or 33. Thus the spring-seated snap-in element 35.2 can be formed as a switching cam which, for example by twisting, is rotated into an intermediate position between the defined positions of rotation for turning on the light. Then the light is switched off in the defined positions of rotation.

In the embodiment shown in FIGS. 6a to 7c, a respective end section of the handle 20 located opposite the head 30 has a function element attached thereto or integrated into it. The function element is a brush 20.4 or a fiber 20.5, connected to an inserting element 20.7, or a light 20.6 integrated into the end piece 20.3, preferably a light-emitting diode, which is directed toward the free end of the handle 20 and in the switched-on state emits light through it. But any other mechanical or electrical function element is also conceivable, in particular a stimulating device. For inserting the end piece 20.3, the inserting element 20.7 is pushed into a matched insert bore 20.8, arranged in the adjoining section of the handle 20, and is fixed in place by clamping, snapping-in or screwing.

If the light 20.6 is integrated into the end piece 20.3, a contact element 21 can be housed in the adjoining section of the handle 20, in particular in the insert bore 20.8, through which an electrical connection is made to an energy supply device, for example a battery 23, also housed in this end section of the handle. For this purpose the battery 23 is housed in a battery receptacle, which can be opened, for example by opening along an indicated division line, for exchanging the battery. A switching element 22 is integrated into a connecting line 24 between the battery 23 and the contact element 21, which can be manually operated from the outside of the handle 20 for switching on or off.

What is claimed is:

1. A plexor, comprising:
   a handle including a ring-shaped holding section at a handle end;
   a head including opposing tapping elements, one of the tapping elements terminating in a line-shaped tapping section, and an other of the tapping elements terminating in a point-like tapping section, each of the opposing tapping elements seated on a receiving body that is partially seated in the ring-shaped holding section;
   the receiving body of the line-shaped tapping section being rotatably seated in the ring-shaped holding section, wherein the line-shaped tapping section is rotatable and fixable in place at each of different angular positions around an axis extending in a longitudinal direction of the head, each of the angular positions defined by at least one of a plurality of grooves cut into an inner surface of the ring-shaped holding section, the grooves being offset from each other by an angle of rotation.

2. In the plexor in accordance with claim 1, wherein one of a clamping mechanism and a snap-in mechanism is provided for fixing the line-shaped tapping section.

3. In the plexor in accordance with claim 2, wherein the grooves are engaged by at least one snap-in element which in an appropriate rotated position is seated on the receiving body and is resiliently pushed outward, and at least one of the grooves and the snap-in element has one of beveled and rounded flanks.

4. In the plexor in accordance with wherein the clamping mechanism has a screw which is fixed on the holding section and by which an inner radius of the holding section is reduced for turning through the holding section for support on the receiving body.

5. In the plexor in accordance with claim 4, wherein the receiving body is assembled from two partial receiving bodies, and one of the partial receiving bodies has an axially oriented central holding pin and the other of the partial receiving bodies has a matched holding bore, and the two partial receiving bodies are connected with each other at least near the holding pin and the holding bore, by being one of pressed together, screwed together and glued together.

6. In the plexor in accordance with claim 5, wherein the line-shaped tapping section is one of parallel with respect to a plane defined between the handle and the head and at right angles with respect to the plane.

7. In the plexor in accordance with claim 6, wherein the receiving body is made of metal and has two detent rings arranged in relation to the longitudinal axis of the head and are spaced apart from each other.

8. In the plexor in accordance with claim 7, wherein a hollow space is formed in the head into which at least one function element is insertable.

9. In the plexor in accordance with claim 8, wherein the at least one function element is at least one of a weight element and an illumination unit.

10. In the plexor in accordance with claim 9, wherein the hollow space is arranged at least partly in an interior of at least one of the holding section and the receiving body.

11. In the plexor in accordance with claim 10, wherein the illumination unit has an electrical energy supply unit and a light source, a manually operable switching member integrated into the head is interspersed in a connecting line between the energy supply unit and the light source, and the light source emits light in a direction of a head element, and the head element is one of removable and transparent.

12. In the plexor in accordance with claim 11, wherein a free end section of the handle facing away from the head is formed as a removable end piece with a function element one of attached to it and integrated into it and is one of removably plugged, screwed and snapped to the adjoining portion of the handle.

13. In the plexor in accordance with claim 12, wherein the function element is one of a brush, a single fiber, and a light, wherein the light is connectible to an electrical energy source inserted into the handle and can be manually switched on via a switching element arranged on the handle.

14. In the plexor in accordance with claim 1, wherein the receiving body is assembled from two partial receiving bodies, and one of the partial receiving bodies has an axially oriented central holding pin and the other of the partial receiving bodies has a matched holding bore, and the two partial receiving bodies are connected with each other at least near the holding pin and the holding bore, by being one of pressed together, screwed together and glued together.

15. In the plexor in accordance with claim 1, wherein the line-shaped tapping section is one of parallel with respect to a plane defined between the handle and the head and at right angles with respect to the plane.

16. In the plexor in accordance with claim 1, wherein the receiving body is made of metal and has two detent rings arranged in relation to the longitudinal axis of the head and are spaced apart from each other, with a circumferential side being flush with a respectively adjoining circumferential side of the tapping elements.

17. In the plexor in accordance with claim 1, wherein a hollow space is formed in the head into which at least one function element is insertable.

18. In the plexor in accordance with claim 8, wherein the hollow space is arranged at least partly in an interior of at least one of the holding section and the receiving body.

* * * * *